United States Patent [19]

Bengsch

[11] Patent Number: 5,580,297
[45] Date of Patent: Dec. 3, 1996

[54] ROYAL JELLY

[75] Inventor: Eberhard Bengsch, Olivet, France

[73] Assignee: GSF-Forschungszentrum für Umwelt und Gesundheit GmbH, Oberschleissheim, Germany

[21] Appl. No.: 396,611

Related U.S. Application Data

[63] Continuation-in-part of PCT/EP93/02562, Sep. 22, 1993.

[22] Filed: Mar. 1, 1995

[30] Foreign Application Priority Data

Sep. 30, 1992 [DE] Germany ............ 42 32 732.6

[51] Int. Cl.⁶ .................................. A01K 47/00
[52] U.S. Cl. ................................ 449/2
[58] Field of Search ............... 449/1, 2; 424/539

[56] References Cited

U.S. PATENT DOCUMENTS 4,405,602  9/1983  Ilies ............ 424/539

FOREIGN PATENT DOCUMENTS 838448  6/1960  United Kingdom.

OTHER PUBLICATIONS

HU–T052942 Derwent 90–337 281.

JP2–152925A. In:. Patents Abstracts of Japan, Sect C, vol. 14, 1990 No. 403 (C–753), pub. 12 Jun. 1990.

Jp. 59–224659 A. ibid. vol. 9, 1985, No. 91 (C–277), pub. 17 Dec. 1984.

*Primary Examiner*—Robert P. Swiatek
*Attorney, Agent, or Firm*—Klaus J. Bach

[57] ABSTRACT

In a method of extracting royal jelly from comb cells of queens, workers, and drones of *Apis mellifera*, the royal jelly is extracted under an inert gas cover such that it does not come into contact with air in the process, whereby the properties of the royal jelly are consistently retained.

4 Claims, No Drawings

ROYAL JELLY

This is a Continuation-in-Part application of International Application PCT/EP93/02562 filed Sep. 22, 1993 claiming the priority of German application P 42 32 732.6 of Sep. 30, 1992.

BACKGROUND OF THE INVENTION

The invention resides in a standardized Royal Jelly, a method of its extraction and the use thereof.

It is known that the workers of *Apis mellifera* generate, between their $9^{th}$ and $15^{th}$ days of life, a milk-like protein-rich feed juice (royal jelly) in their hypopharyngal glands and especially in the middle mandibular gland. This feed juice is used in small amounts for the original feeding of the whole breed in the egg-containing cells, (worker and drone cells). It is supplied in substantial amounts to the cell in which a queen is to develop whose only purpose is to reproduce. Royal jelly is the only food fed to the queen and is completely metabolized by her without excretion. It protects the queen from infection and gives her a life span of 50 times that of normal bees (inspite of the fact that her genes are identical to those of the worker bees). It also endows her with enormous reproductive capacity; up to two million offspring from the initial fertilization.

Royal jelly is also known to have interesting therapeutic effects on vertebrates, particularly in mammals and humans, such as:

protection from infections caused by gram-positive and gram-negative bacteria.

antitumor and antiviral effects, essentially without any zytotoxic effects on the host tissue.

There is considerable interest in processes for extracting substantial amounts of royal jelly for commercial distribution of the raw substance or stabilized forms prepared therefrom, as well as for the research and isolation of many effective substances which are generally unknown and which are present only in traces.

It has been found, however, that the therapeutic effects described above are altogether or partially uncertain; particularly the antiviral effects have been found to be limited and not clearly reproducible in-vitro or in-vivo. Different results have been obtained, even from the same substance sample. The impossibility to transfer from one testing system to another limits the research capabilities. The random, spectacular results achieved in clinical tests, particularly in cancer research, prove to be inconsistent. This inconsistency and non-transferability resulted in the discrediting of royal jelly, both as a therapeutic raw substance as well as a research substance in the search for new effective substances and their commercialization.

The inventor has found however, that suprisingly, the reason for the varying effects and losses of effects of the effective substances is not so much the result of deterioration caused by storage of the substances as it is caused by the extraction process presently in use.

For the gathering of royal jelly, the bee combs are provided with separation grids for the queen and with queen cell structures containing almost two dozen artificial queen cells. After 72 hours, the queen larvae are removed from the queen cells. The remaining milky suspension is sucked out in a rapid procedure by sucking in air via a narrowed tube and is directed onto a receptacle wall. The vacuum for this procedure is generated by a central pump which is capable of serving several work locations. The pump has a substantial suction capacity (like pumps for bovine milking machines). This results in a large volume of air passing through completely atomizing the milky royal jelly material. With extraction quantities being so minute (only 300 mg/queen cell), the extraction process and subsequent handling expose the raw substance to varying amounts of oxygen. This relationship is particularly detrimental in the extraction of the raw substance from worker and drone cells (containing only 10 mg/cell).

It is the object of the present invention to provide a method of gathering standardized royal jelly with consistently high antiviral properties and optimized other effectiveness.

SUMMARY OF THE INVENTION

In a method of extracting royal jelly from comb cells of queens, workers, and drones of *Apis mellifera*, the royal jelly is extracted under an inert gas cover such that it does not come into contact with air and oxygen in the process.

In this manner, exposure of the raw royal jelly substance to air and oxygen is eliminated. Preferably extraction and collection of the raw product is realized in a closed system under an argon gas protective cover or another inert gas (such as nitrogen, $CO_2$, helium, fluorochlorohydrocarbons, krypton).

DESCRIPTION OF AN EXEMPLARY EMBODIMENT

In a preferred embodiment of the invention, 10–100 queen cell strips each having about 20 cells, in which a brood has started to develop, are placed in a box including a protective gas. The box includes a pair of gloves for remote handling from outside, a controllable suction pump, a collection receptacle, a PTFE (polytetrafluorethylene) hose, and a suction pipe. Through a valve opening in the lower part of the glove box, the protective gas, preferably argon, is admitted to the box while gas discharged from a valve opening in the upper part of the box, is conducted via a hose into a small cylindrical container, at the bottom of which a burning candle is disposed. Extinguishing of the candle indicates that argon completely fills the box. The extraction of the royal jelly from the queen cells or other cells is then performed in a fully closed system. Argon fills the box and serves as the suctioning gas which is recirculated into the box so that the substance being extracted comes into contact only with the argon gas. This procedure is more time-consuming, but the additional time and effort requirements incurred with the method according to the invention are within reasonable limits. In order to reduce these requirements, it is proposed to automate the procedure and/or perform the extraction procedure under the control of a microprocessor by means of a procedure as used for example with sample changers for chemical, spectrochemical, and chromatographic methods.

The substances obtained by this method according to the invention were tested for antiviral effectiveness with a system of Hela cells/ Coxsackie-B3 virus. The royal jelly obtained in accordance with the invention under an inert protective gas provided in each of five tests for a total virus titer reduction. Five comparative tests with royal jelly obtained in accordance with prior art procedures from queen cells of the same bee colony showed only a slight reduction in three cases and no difference from the untreated cell culture in two cases. The non-reproducibility of antiviral effects of royal jelly obtained in accordance with the prior art procedure is essentially eliminated by the process according to the invention. Furthermore, it has been found that the product as obtained by the method according to the invention exhibits an improved solubility in a hydrophile environment. This is believed to provide for faster and better absorbability in the stomach and intestinal tract.

Chemical tests show that also in vivo, the antiviral effects (on Hepatitis B, HBV, Herpes HVH types 1 and 2) as well as other therapeutic properties of the royal jelly raw substance, are substantially improved and that a highest-quality product with optimal overall properties is obtained by the method according to the invention.

It has further been found that a timely limited surface contact of the liquid royal jelly with air does not lead to a reduced effectiveness so that bottling and processing of the royal jelly in open air is possible and that an inert cover gas, although desirable, is not necessary.

What is claimed is:

1. In a method of extracting royal jelly from comb cells of queens, workers and drones of *Apis mellifera*, the improvement, wherein extraction takes place under an inert gas cover.

2. A method according to claim 1, wherein the inert gas utilized is heavier than air.

3. A method according to claim 2, wherein said inert gas is argon.

4. A method according to claim 2, wherein extraction of said royal jelly is performed by an automated micro-processor-controlled process.

* * * * *